(12) United States Patent
Krag

(10) Patent No.: US 6,231,575 B1
(45) Date of Patent: May 15, 2001

(54) SPINAL COLUMN RETAINER

(76) Inventor: Martin H. Krag, 25 Crooked Creek Rd., Colchester, VT (US) 05446

(*) Notice: Subject to any disclaimer, the term of this patent is extended or adjusted under 35 U.S.C. 154(b) by 0 days.

(21) Appl. No.: 09/375,148

(22) Filed: Aug. 16, 1999

Related U.S. Application Data

(60) Provisional application No. 60/098,071, filed on Aug. 27, 1998.

(51) Int. Cl.[7] ................................................. A61B 17/70
(52) U.S. Cl. .............................................................. 606/61
(58) Field of Search ........................................ 606/61, 73

(56) References Cited

U.S. PATENT DOCUMENTS

| 4,987,892 | | 1/1991 | Krag et al. . | |
|---|---|---|---|---|
| 5,002,542 | | 3/1991 | Frigg . | |
| 5,053,034 | | 10/1991 | Olerud . | |
| 5,129,900 | | 7/1992 | Asher et al. . | |
| 5,254,118 | | 10/1993 | Mirkovic . | |
| 5,257,993 | | 11/1993 | Asher et al. . | |
| 5,261,909 | | 11/1993 | Sutterlin et al. . | |
| 5,306,275 | | 4/1994 | Bryan . | |
| 5,403,316 | | 4/1995 | Ashman . | |
| 5,487,744 | * | 1/1996 | Howland | 606/61 |
| 5,582,612 | * | 12/1996 | Lin | 606/61 |
| 5,741,255 | | 4/1998 | Krag et al. . | |
| 5,743,907 | * | 4/1998 | Asher et al. | 606/73 |
| 5,776,135 | * | 7/1998 | Errico et al. | 606/61 |
| 5,879,351 | * | 3/1999 | Vlart | 606/61 |
| 6,050,997 | * | 4/2000 | Mullane | 606/61 |

* cited by examiner

Primary Examiner—Paul J. Hirsch
(74) Attorney, Agent, or Firm—Barnes & Thornburg

(57) ABSTRACT

A spinal column retainer including a rod for positioning along a spinal column, a fastener having a first portion for screwing into a portion of the spinal column and a second portion for receiving a nut, a retainer block including a passage for receiving the rod, a threaded passage for receiving a set screw, and a transverse passage, and an angular member extending between the retainer block and the fastener. The angular member has an inner end portion captured within the retainer block, an outer end portion secured to the fastener, and a connecting portion between the end portions which forms an angular bend to offset the outer end portion from an axis of the inner end portion. The set screw forces the rod against the angular member which is forced against the retainer block, preventing movement of the components relative to one another.

20 Claims, 5 Drawing Sheets

SPINAL COLUMN RETAINER

This application claims benefits of provisional application 60/098,071 field Aug. 27, 1998.

BACKGROUND OF THE INVENTION

The present invention relates to an apparatus for retaining portions of a spinal column, such as vertebrae, in a desired spatial relationship. Specifically, the present invention relates to retainers of the type disclosed in U.S. Pat. No. 5,741,255, issued Apr. 21, 1998, and in the prior art references cited therein, all of which are incorporated herein by reference.

SUMMARY OF THE INVENTION

The present invention provides an apparatus for retaining portions of a spinal column in a desired spatial relationship. The apparatus generally includes a threaded fastener which engages a portion of the spinal column and a longitudinal member or rod which is positioned along the spinal column at a location offset from the fastener. An angular member is connected between the fastener and the rod and extends for a first distance in a direction away from the rod and for a second distance in a direction at an angle relative to the first direction.

A retainer assembly is connected to the rod and the angular member and retains the rod and angular member against movement relative to the retainer assembly. The retainer assembly includes a retainer block into which the rod and the angular member extend. The retainer assembly is effective to hold the rod and the angular member against movement relative to the block due to force transmitted between the rod and the angular member. In one embodiment of the invention, the above-described force is transmitted between the rod and the angular member by pressing them against one another using an engagement member which, in one embodiment is a set screw.

The angular member may be provided with retaining surfaces which are engaged by mating surfaces on the block. The retaining surfaces and the mating surfaces cooperate to prevent rotational movement of the angular member about a central axis extending through the end portion of the angular member held by the block. The angular member may be formed to bend at a right angle between the block and the fastener. In one embodiment of the invention, a section of the angular member extends in a first direction parallel to the rod when the retaining surfaces and mating surfaces are engaged. In an alternate embodiment, a section of the angular member extends in a direction opposite the first direction when the retaining surfaces and mating surfaces are engaged.

BRIEF DESCRIPTION OF THE DRAWINGS

The foregoing and other features of the invention will become more apparent and the invention will be better understood upon consideration of the following description taken in conjunction with the accompanying drawings, wherein.

DETAILED DESCRIPTION OF EMBODIMENTS OF THE INVENTION

Figure 1:
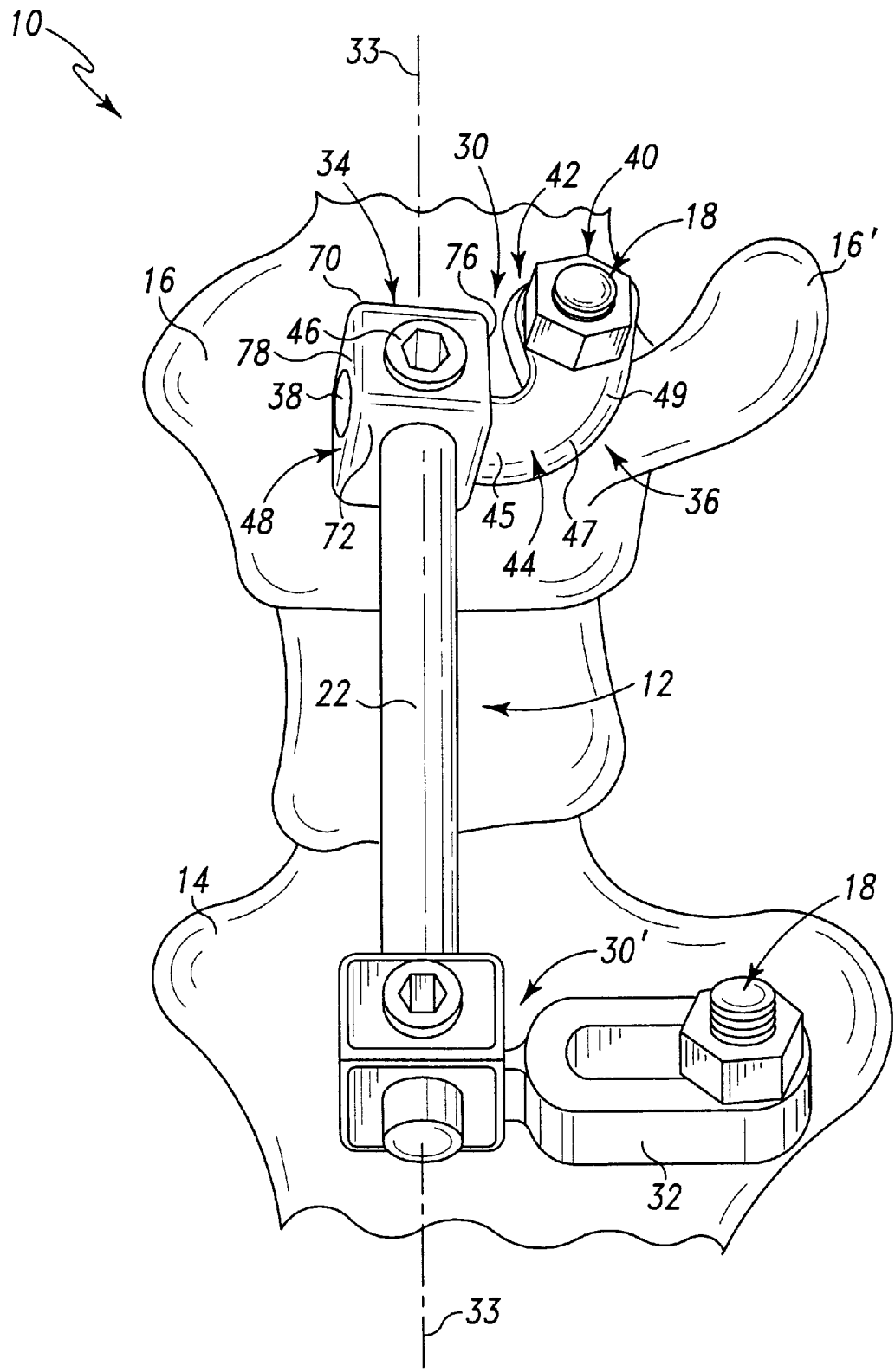
FIG. 1 is a dorsal view of a portion of a spinal column with a spinal column retainer according to the present invention to maintain a desired spatial relationship between vertebrae of the spinal column.

A portion of a human spinal column 10 to which spinal column retainer 12 is attached is illustrated in FIG. 1. Spinal column retainer 12 positions vertebrae 14, 16 in a desired spatial relationship relative to one another.

Spinal column retainer 12 includes fasteners 18 made of a biocompatible material, such as stainless steel. As described in greater detail below, fasteners 18 include first threaded portions 20 (FIG. 2) which engage vertebrae 14, 16 to fixedly mount the fasteners to the vertebrae. It should be understood that multiple fasteners 18 may be secured to each vertebrae 14, 16 where multiple spinal column retainers 12 are used. Although FIG. 1 shows spinal column retainer 12 configured to space two vertebrae 14, 16 relative to one another, it should be understood that many more vertebrae may be retained in spatial relationship to one another by simply increasing the length of the rod 22 extending along spinal column 10 and attaching additional connector assemblies 30 between rod 22 and the additional vertebrae.

Rod 22 is made of a biocompatible material, such as stainless steel. As indicated above, rod 22 has a length sufficient to enable the rod to span at least two vertebrae 14, 16. The required length of rod 22 depends upon the condition to be treated and the number of vertebrae to be held in a desired spatial relationship relative to one another. Rod 22 may be bent as desired, typically to establish a desired curvature of spinal column 10 in all or any of three possible anatomic planes.

FIG. 1 shows two types of connector assemblies (30 and 30') for interconnecting rod 22 and fasteners 18. The lower connector assembly 30' is of the kind described and shown in U.S. Pat. No. 5,741,255. As fully explained in U.S. Pat. No. 5,741,255, connector assembly 30' includes a transverse member 32 which extends between fastener 18 and rod 22 in perpendicular relationship to a longitudinal axis 33 of rod 22. The connector assembly 30 of the present invention (the upper connector assembly shown in FIG. 1) generally includes a retainer assembly 34 which is mounted on rod 22, and an angular member 36 which extends between fastener 18 and retainer assembly 34. Retainer assembly 34 fixes the position of a generally cylindrical inner end portion 38 of angular member 36 relative to retainer assembly 34. A clamp assembly 40 fixedly connects an outer end portion 42 of the angular member 36 to fastener 18. In one embodiment of the invention, a connecting portion 44 forms a right angle bend between inner end portion 38 and outer end portion 42 of angular member 36.

Figure 2:
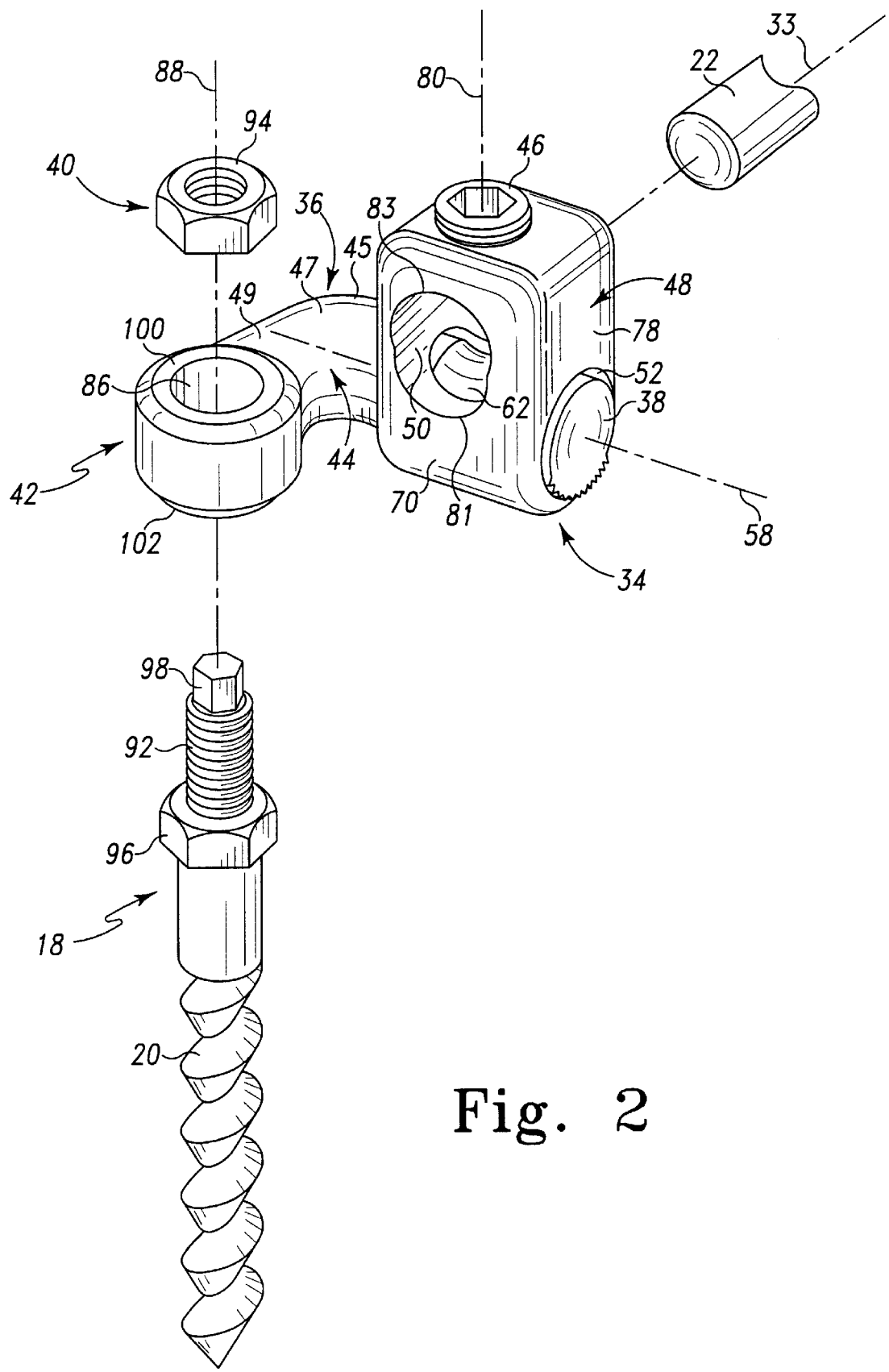
FIG. 2 is a fragmentary, exploded, perspective view of a spinal column retainer according to the present invention.
Figure 6:
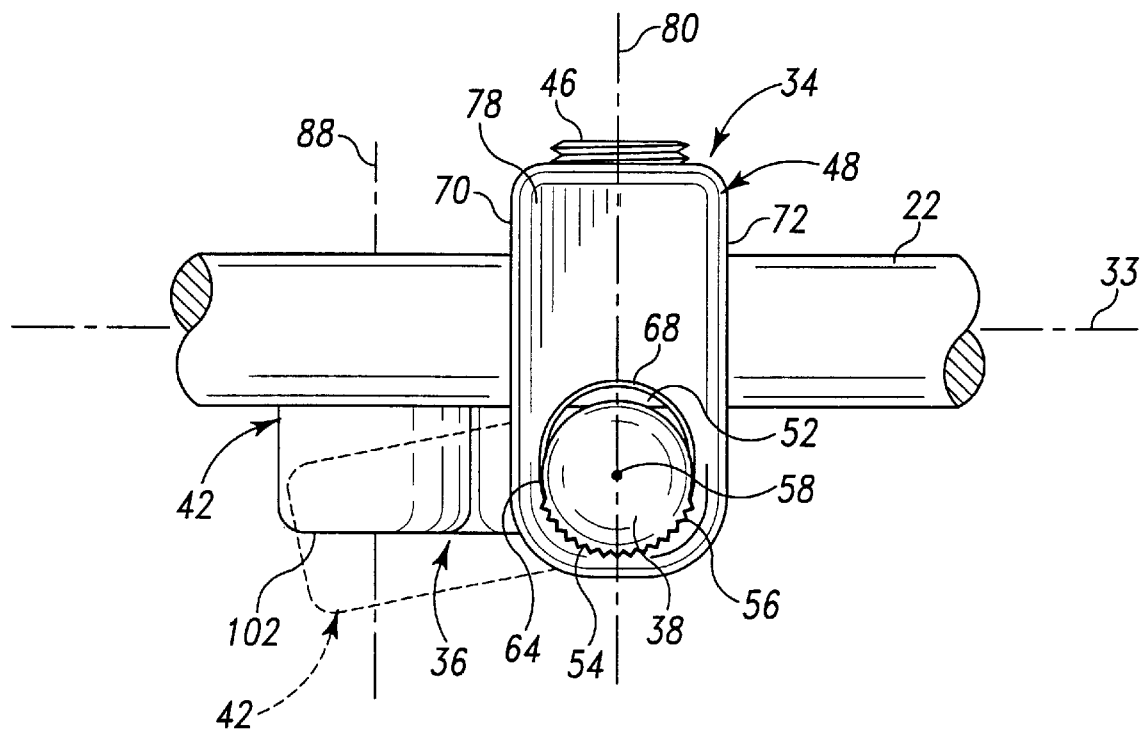
FIG. 6 is another side elevational view of the apparatus of FIG. 3.

Referring now to FIG. 2, retainer assembly 34 includes a set screw 46 and a generally rectangular retainer block 48 into which angular member 36 and rod 22 extend. Block 48 has a rod passage 50 which receives rod 22. Rod 22 is shown having a substantially circular cross-section; however, rods having various other cross-sections, such as hexagonal or oval cross-sections, could be used with corresponding modifications to rod passage 50. Block 48 also includes a transverse passage 52 which receives inner end portion 38 of angular member 36 and communicates with rod passage 50. As best shown in FIG. 6, transverse passage 52 includes a plurality of mating surfaces 54 which engage similarly shaped retaining surfaces or teeth 56 that project radially outwardly from inner end portion 38 of angular member 36. Meshing engagement between mating surfaces 54 on block 48 and teeth 56 on inner end portion 38 prevents rotational movement of angular member 36 about a longitudinal central axis 58 of inner end portion 38. It is understood that mating surfaces of various shapes may be formed in transverse passage 52 to receive similarly shaped retaining surfaces formed on block 48. For example, the triangular teeth shown in FIG. 6 may be replaced with rectangular ridges and mating channels or curved protrusions and mating grooves.

Figure 7:
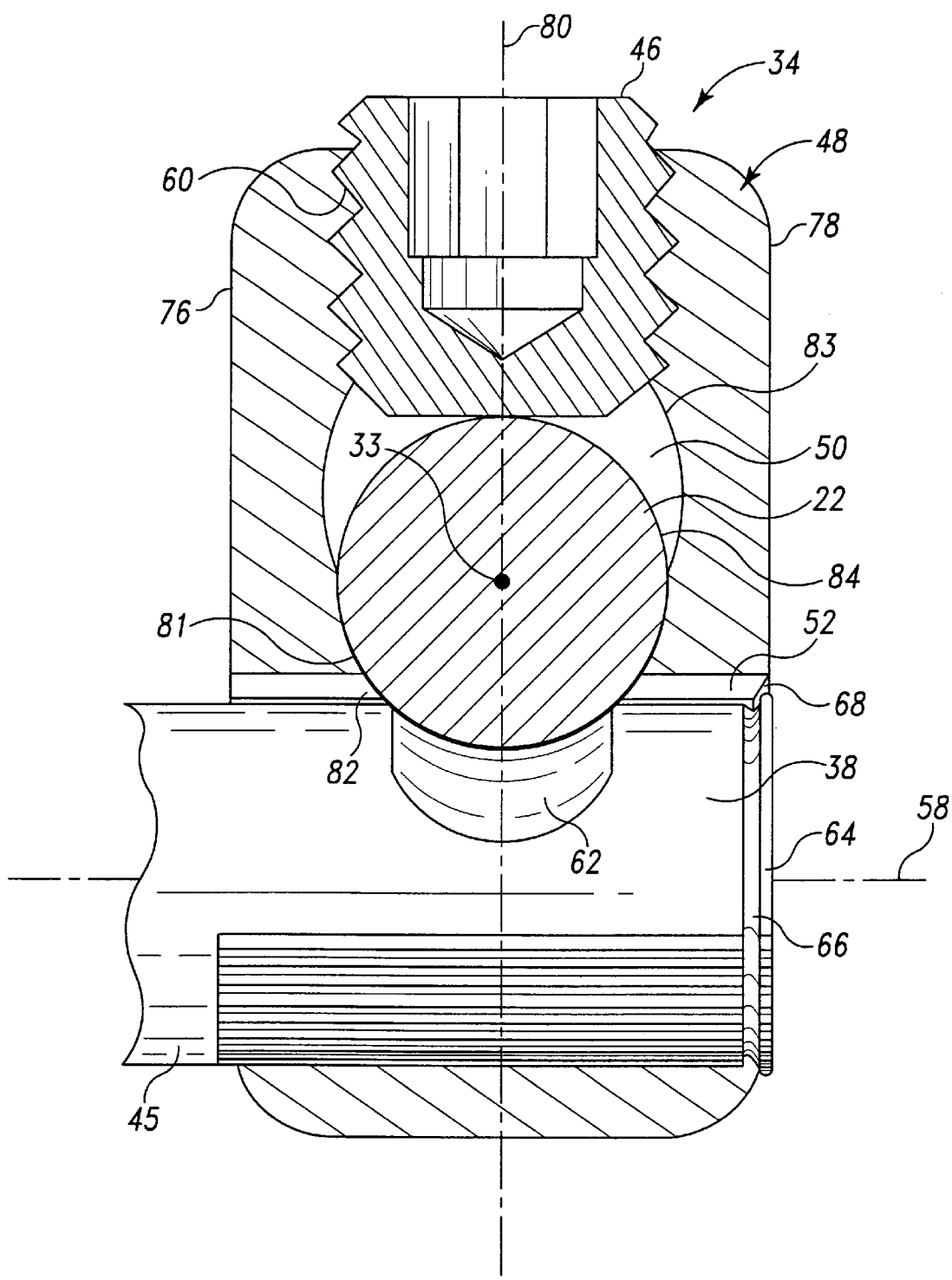
FIG. 7 is a fragmentary sectional view taken substantially along lines 7—7 of FIG. 3.

As best shown in FIG. 7, force is transmitted between rod 22 and angular member 36 by set screw 46 to hold rod 22 and angular member 36 against movement relative to block 48. Set screw 46 is tightened into threaded set screw passage 60 which is formed in block 48 and communicates with rod passage 50. Set screw 46 moves downwardly into engagement with rod 22, thereby forcing rod 22 downwardly against inner end portion 38 of angular member 36. Specifically, rod 22 is urged downwardly into a saddle-shaped groove 62 which extends partially around the circumference of inner end portion 38. Groove 62 is formed to receive the curved outer surface 84 of rod 22. The force transmitted by rod 22 presses teeth 56 of inner end portion 38 into meshing engagement with mating surfaces 54 of the lower portion of transverse passage 52 (FIG. 6). Accordingly, engagement between the outer surface 84 of rod 22 and groove 62 of inner end portion 38 retains inner end portion 38 against movement relative to block 48 about central axis 58 and retains rod 22 against movement relative to block 48 along longitudinal axis 33.

Inner end portion 38 of angular member 36 further includes an annular lip 64 and a circumferential groove 66 formed, for example, by a swaging operation. Annular lip 64 is formed such that its outer diameter is larger than an inner diameter of transverse passage 52 (FIG. 6). Accordingly, angular member 36 is retained within retainer assembly 34 even when rod 22 is removed or raised upwardly within rod passage 50. Additionally, one end of transverse passage 52 includes a beveled edge 68 (FIG. 7) which permits recess of annular lip 64 within transverse passage 52.

Figure 3:
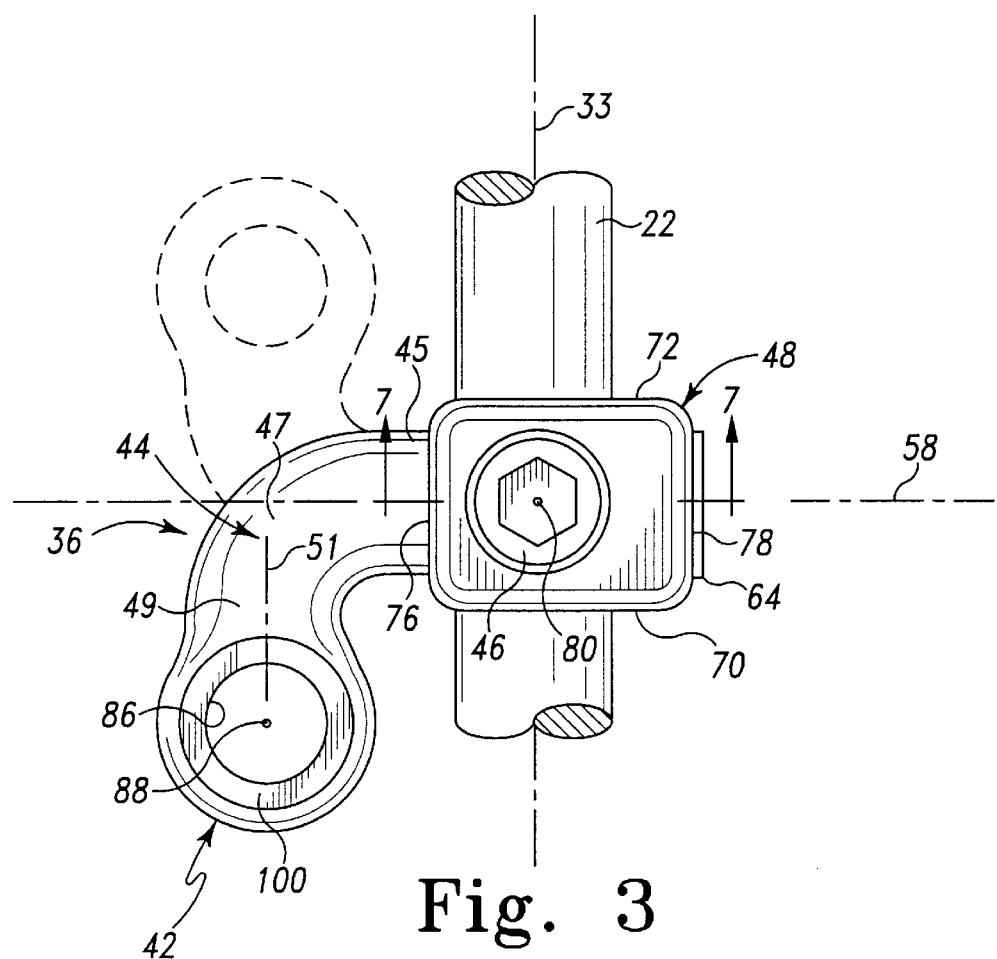
FIG. 3 is a fragmentary top plan view of components of a spinal column retainer according to the present invention.
Figure 4:
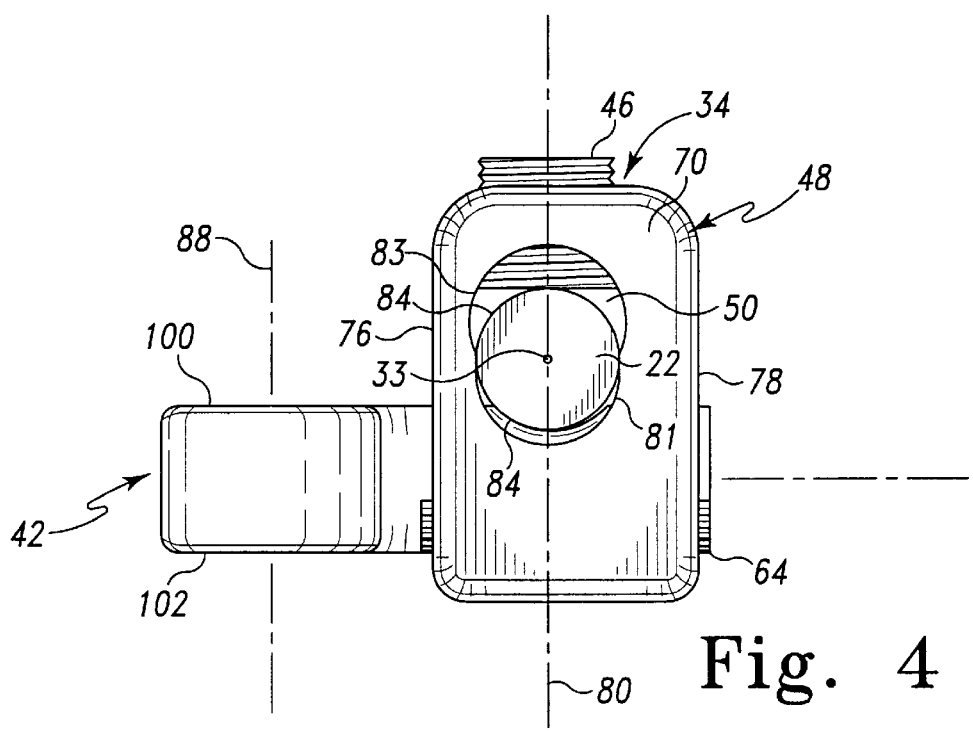
FIG. 4 is a side elevational view of the apparatus of FIG. 3.

Referring now to FIGS. 2–4, block 48 has a pair of parallel, flat side surfaces 70, 72. Rod passage 50 extends between and is perpendicular to side surfaces 70, 72. Block 48 also includes a pair of parallel side surfaces 76, 78 which extend perpendicular to side surfaces 70, 72 (FIG. 3). Transverse passage 52 has a straight longitudinal central axis which extends between and is perpendicular to side surfaces 76, 78.

Rod passage 50 is formed by a pair of circular openings 81, 83 having centers which are offset along an axis 80 (FIGS. 2, 4, and 7) of block 48. As a result, rod passage 50 has a generally oval cross-sectional configuration. In one embodiment of the present invention, axis 80 is substantially centered between sides 70, 72, but is closer to side 76 than side 78 of block 48. Circular openings 81, 83 which form rod passage 50 are sized such that rod 22 can move between the upper and lower portion of rod passage 50 when set screw 46 is backed out of set screw passage 60. Accordingly, block 48 may be positioned along the length of rod 22. As best shown in FIG. 7, upper circular opening 83 is larger than the diameter of rod 22 so that rod 22 can move freely within opening 83. Lower circular opening 81 of rod passage 50 has a diameter which is smaller than the diameter of rod 22. Thus, rod 22 and rod passage 50 have an interference fit when rod 22 is urged into lower circular opening 81 by set screw 46.

As best shown in FIG. 6, transverse passage 52, like rod passage 50, has a generally oval cross-section which is elongated in the direction of axis 80 of block 48. The oval configuration of transverse passage 52 enables movement of inner end portion 38 of angular member 36 upwardly and downwardly along central axis 80 when set screw 46 is backed out of set screw passage 60.

The orientation of angular member 36 relative to block 48 may be adjusted by moving end portion 38 upwardly within transverse passage 52 to space teeth 56 from mating surfaces 54 so that inner end portion 38 may be rotated within transverse passage 52 about axis 58 to a desired position relative to block 48 and rod 22 (an example position is shown in dotted lines in FIG. 6). After angular member 36 is rotated into a desired orientation about axis 58, inner end portion 38 is moved downwardly (by set screw 46 and rod 22) so that teeth 56 engage mating surfaces 54 of block 48, thereby preventing further rotation of angular member 36.

Transverse passage 52 and rod passage 50 form an intersection 82 (FIG. 7) in a central portion of block 48. Accordingly, a portion of transverse passage 52 extends into rod passage 50. In one embodiment of the invention, rod passage 50 has a central axis which is perpendicular to the central axis of transverse passage 52. In such an embodiment, when spinal column retainer 10 is assembled, axis 58 of inner end portion 38 is perpendicular to longitudinal axis 33 of rod 22 (FIG. 3). It should be understood, however, that transverse passage 52 and rod passage 50 could be formed at an acute angle relative to one another. In such a configuration, inner end portion 38 of angular member 36 would extend from block 48 at an acute angle relative to axis 33 of rod 22.

When block 48 is positioned on rod 22, the rod extends into intersection 82 (FIG. 7) between rod passage 50 and transverse passage 52. Thus, the outer side surface 84 (FIGS. 4 and 7) of rod 22 may be forced against curved groove 62 of inner end portion 38 by set screw 46. Consequently, inner end portion 38 is pressed against the lower portion of block 48 by rod 22 (best shown in FIG. 6). It should be understood that an intermediate force transmitting member could be positioned between outer side surface 84 and inner end portion 38.

Mating surfaces 54 of block 48 (FIG. 6) are disposed on a side of transverse passage 52 opposite from intersection 82. Mating surfaces 54 extend between side walls 76 and 78 of block 48, parallel to central axis 58 of inner end portion 38. Mating surfaces 54 are formed along an arc of transverse passage 52 and extend approximately 30 degrees on each side of axis 80 of block 48. Accordingly, mating surfaces 54 have a total arcuate extent of approximately 60 degrees.

Similarly, each of teeth 56 on inner end portion 38 has a longitudinal axis which extends parallel to central axis 58 of inner end portion 38. Teeth 56 have an arcuate extent of approximately 120° about the lower outer surface of inner end portion 38. Teeth 56 may, of course, be formed such that they cover more or less than 120° of the outer surface of inner end portion 38. Since the arcuate extent of teeth 56 on inner end portion 38 is greater than the arcuate extent of mating surfaces 54 of block 48, teeth 56 can meshingly engage mating surfaces 54 when angular member 36 is in any one of a plurality of rotational orientations about axis 58 relative to block 48, as described above.

In one embodiment of the invention, angular member 36 may be provided in a "right" configuration or a "left"

configuration. A "right" configuration angular member 36 is shown in the figures. As viewed in FIG. 1, angular member 36 extends to the right of block 48 (away from side 76 of block 48) and upwardly, away from side 72 of block 48. As should be apparent from the foregoing, the entire connector assembly 30 could be removed from rod 22, rotated 180°, and reinstalled on rod 22 (FIG. 3) such that angular member 36 extends to the left of block 48 (away from side 76) and downwardly, away from side 72. While the orientation of angular member 36 relative to block 48 may be rotationally adjusted somewhat about axis 58, the angular member 36 shown in FIG. 3 cannot be rotated 180° about axis 58 such that it extends to the left of block 48 and upwardly into the orientation provided by a "left" configuration angular member (shown in dotted lines). As shown in FIGS. 6 and 7, such adjustment of "right" configuration angular member 36 is not possible because, if rotated about axis 58 180° out of the position shown in FIGS. 6 and 7, teeth 56 of angular member 36 would face upwardly toward rod 22 and groove 62 would face downwardly toward mating surfaces 54 of block 48. Accordingly, rod 22 and groove 62 could not cooperate to fix the position of angular member 36 along axis 58 relative to block 48, and teeth 56 and mating surfaces 54 could not cooperate to fix the orientation of angular member 36 about axis 58 relative to block 48. Thus, a "left" configuration angular member according to the present invention includes an inner end portion 38 identical to that shown in the figures, but extends away from side 76 of block 48 and upwardly, away from side 70 when block 48 is fastened to rod 22 in the orientation shown in FIG. 3.

A universal angular member 36 could readily be made by, for example, forming groove 62 around the entire circumference of inner end portion 38 and forming teeth 56 on the remainder of the surface of inner end portion 38 not occupied by groove 62. Although the meshing surface area between teeth 56 and mating surfaces 54 would be reduced, such a retainer member 36 could be adjusted to any one of a plurality of angular orientations within a 360° range of adjustment about axis 58. Alternatively, the arcuate extent of teeth 56 could be reduced from 360° and the arcuate extent of mating surfaces 54 could be increased such that a sufficient number of teeth 56 engage a sufficient number of mating surfaces 54 at any one of a plurality of angular orientations within a 360 range of adjustment about axis 58.

In one embodiment of the invention, outer end portion 42 of angular member 36 is generally cylindrical in shape and includes a bore 86. Bore 86 has a central axis 88 which is perpendicular to central axis 58 of inner end portion 38 (FIG. 2). Fastener 18 is received by bore 86. When angular member 36 is secured to fastener 18 as described below, central axis 88 of bore 86 may be coincident with a central axis of fastener 18. Thus, fastener 18 may extend in a direction perpendicular to central axis 58 of inner end portion 38. However, as best shown in FIG. 3, central axis 88 of bore 86 is offset a distance from central axis 58 and a distance from axis 33 of rod 22.

Referring now to FIG. 2, a clamp assembly 40 is formed by a threaded outer end portion 92 of fastener 18, an internally threaded nut 94, a hexagonal shoulder 96 formed on fastener 18, and a hexagonal outer end portion 98. By simultaneously engaging hexagonal outer end portion 98 and nut 94 with wrenches, nut 94 may be firmly tightened onto threaded portion 92 of fastener 18 without transmitting force to threaded portion 20 of fastener 18. When nut 94 is tightened, it engages the upper end surface 100 of outer end portion 42, and shoulder 96 engages the lower end surface 102 of outer end portion 42. Consequently, outer end portion 42 is held fixed relative to fastener 18 by clamp assembly 40.

Figure 5:
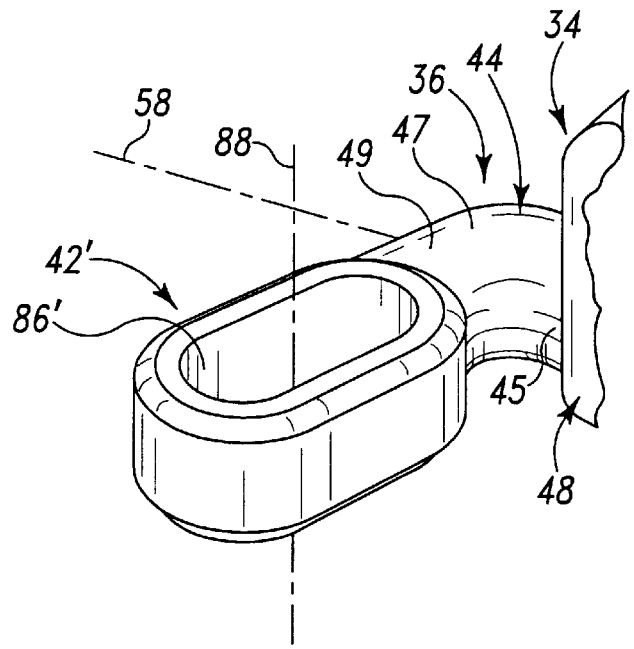
FIG. 5 is a fragmentary perspective view of an alternate embodiment of a component of the present invention.

FIG. 5 shows an alternate embodiment of outer end portion 42 of angular member 36 (designated 42'). Outer end portion 42' includes a slot 86' instead of bore 86. Slot 86' is, in this embodiment, elongated in a direction substantially perpendicular to central axis 58 of inner end portion 38 and has a central axis 88 which is substantially perpendicular to axis 58. Outer end portion 42' otherwise cooperates with fastener 18 in the manner described above. As should be apparent from the foregoing, the elongated configuration of slot 86' permits adjustment of the distance between fastener 18 and axis 58.

Connecting portion 44 of angular member 36 extends between inner end portion 38 and outer end portion 42. Connecting portion includes a first section 45 which extends from inner end portion 38, a second section 47 which extends from first section 45, and a third section 49 which extends between second section 47 and outer end portion 42. In one embodiment, connecting portion 44 is tubular or bar-shaped and first, second, and third portions 45, 47, 49 and substantially planar. First section 45 extends away from block 48 and is centered on axis 58 (FIG. 3). Second section 47 forms an angular bend or elbow away from axis 58 In the embodiment illustrated, the angular bend of second section 47 is 90°. Alternatively, the angular bend could provide a different angle relative to axis 58, such as a 45° angle. Third section 49 extends along an axis 51 at the angle relative to axis 58 established by second section 47, and connects to outer end portion 42. It should be understood that outer end portion 42 need not be planar relative to connecting portion 44, but rather may extend at an angle relative to a plane intersecting first, second, and third sections 45, 47, 49 of connecting portion 44.

The direction of the angular bend of second section 47 determines whether angular member 36 is a "right" or "left" configuration angular member. As shown in FIG. 1, the angular bend provided by connecting portion 44 permits attachment of connector assembly 30 to a vertebra having a portion 16' which would otherwise interfere with a laterally extending transverse member 32 of a connector assembly 30' (the lower connector assembly). Additionally, where multiple spinal column retainers 12 are used on a single spinal column 10, interference between adjacent connector assemblies 30 may be avoided by the offset location of fastener 18 provided by the angular bend of connecting portion 44.

While this invention has been described as having exemplary embodiments, this application is intended to cover any variations, uses, or adaptions using its general principles. Further, this application is intended to cover such departures from the present disclosure as come within the known or customary practice within the art to which it pertains. The spirit and scope of the invention are to be limited only by the terms of the appended claims.

What is claim is:

1. A spinal column retainer for implantation into a patient to retain portions of a spinal column in a desired spatial relationship relative to one another, comprising:
   a rod;
   a fastener having a first threaded portion for screwing into a portion of the spinal column;
   a block including a first passage for receiving the rod and a second passage in communication with the first passage; and
   an angular member including a first end portion extending into the second passage and having a central axis, a second end portion for connecting to the fastener, and an angular bend between the first end portion and the second end portion, the angular bend spacing the second end portion from the block and the central axis;

the rod being secured to the block and engaging the angular member to prevent movement of the angular member relative to the block.

2. A spinal column retainer according to claim 1 wherein the angular bend is a right angle.

3. A spinal column retainer according to claim 1 further comprising a first section extending between the first end portion and the angular bend and a third section extending between the angular bend and the second end portion.

4. A spinal column retainer according to claim 3 wherein the third section has a central axis which is substantially parallel to a longitudinal axis of the rod.

5. A spinal column retainer according to claim 1 wherein the second passage extends through the block at a right angle relative to the first passage.

6. A spinal column retainer according to claim 1 wherein the first end portion of the angular member includes a groove for receiving the rod, the first passage extending through a first side and a second side of the block, the second passage extending through a third side and a fourth side of the block.

7. A spinal column retainer according to claim 6 wherein the first end portion of the angular member is substantially cylindrical, having a plurality of retaining surfaces projecting radially outwardly relative to the central axis, the plurality of retaining surfaces being disposed on an outer surface of the first end portion substantially opposite the groove, the second passage of the block including a plurality of mating surfaces for receiving the plurality of retaining surfaces when the rod engages the angular member, thereby preventing rotational movement of the angular member about the central axis.

8. A spinal column retainer according to claim 7 further comprising a first section extending between the first end portion and the angular bend and a third section extending between the angular bend and the second end portion.

9. A spinal column retainer according to claim 8 wherein the first section extends from the first end portion away from the third side of the block and the third section extends from the second section away from the first side of the block when the plurality of mating surfaces receive the plurality of retaining surfaces.

10. A spinal column retainer according to claim 8 wherein the first section extends from the first end portion away from the third side of the block and the third section extends from the second section away from the second side of the block when the plurality of mating surfaces receive the plurality of retaining surfaces.

11. A spinal column retainer according to claim 1 wherein the first end portion of the angular member includes a plurality of outwardly projecting retaining surfaces, the second passage of the block including a plurality of mating surfaces for receiving the plurality of retaining surfaces when the rod engages the angular member, thereby preventing movement of the angular member about the central axis.

12. A spinal column retainer according to claim 1 wherein the first end portion of the angular member is substantially cylindrical and includes an annular lip at an end opposite the angular bend to retain the angular member within the block, the annular lip having an outer diameter larger than an inner diameter of the second passage.

13. A spinal column retainer according to claim 12 wherein the second passage includes a beveled edge, the annular lip being at least partially recessed in the second passage by the beveled edge.

14. A spinal column retainer according to claim 1 wherein the second end portion includes an opening for receiving a portion of the fastener.

15. A spinal column retainer according to claim 14 wherein the opening is a bore.

16. A spinal column retainer according to claim 14 wherein the opening is a slot.

17. A spinal column retainer according to claim 1 further comprising a third passage which extends into the block in communication with the first passage, and an engagement member which is received by the third passage and engages the rod to cause the rod 22 to engage the angular member.

18. A spinal column retainer according to claim 17 wherein the third passage is threaded and the engagement member is a set screw.

19. A spinal column retainer for implantation into a patient to retain portions of a spinal column in a desired spatial relationship relative to one another, comprising:

a rod;

a fastener having a first threaded portion for screwing into a portion of the spinal column and a second portion;

a block including a first passage for receiving the rod and a second passage in communication with the first passage; and an angular member including a first end portion extending into the second passage and having a central axis, a second end portion for connecting to the second portion of the fastener, the fastener being secured to the second end portion, and a connecting portion having a first section extending from the first end portion away from the block along the central axis, a second section extending from the first section forming an angular bend away from the central axis, and a third section extending between the second section and the second end portion at an angle relative to the central axis;

the rod being secured to the block and engaging the angular member to prevent movement of the angular member relative to the block.

20. A spinal column retainer for implantation into a patient to retain portions of a spinal column in a desired spatial relationship relative to one another, comprising:

a rod;

a fastener having a first threaded portion for screwing into a portion of the spinal column and a second portion;

a block including a first passage for receiving the rod, a second passage, and a third passage, the second passage and third passage being in communication with the first passage;

an angular member including a first end portion extending into the third passage and having a central axis, a second end portion having an opening for receiving the second portion of the fastener, the fastener being secured to the second end portion, and a connecting portion having a first section extending from the first end portion away from the block along the central axis, a second section extending from the first section forming an angular bend away from the central axis, and a third section extending between the second section and the second end portion at an angle relative to the central axis; and an engagement member for extending into the second passage to engage the rod, thereby preventing movement of the rod relative to the block and causing the rod to engage the angular member to prevent movement of the angular member relative to the block.

* * * * *